US009937007B2

(12) United States Patent
Cooper et al.

(10) Patent No.: US 9,937,007 B2
(45) Date of Patent: Apr. 10, 2018

(54) ANGLED INSTRUMENT SHAFT ROLL ACTUATOR

(71) Applicant: Intuitive Surgical Operations, Inc., Sunnvale, CA (US)

(72) Inventors: Thomas G. Cooper, Menlo Park, CA (US); S. Christopher Anderson, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 887 days.

(21) Appl. No.: 14/458,018

(22) Filed: Aug. 12, 2014

(65) Prior Publication Data

US 2015/0051034 A1 Feb. 19, 2015

Related U.S. Application Data

(60) Provisional application No. 61/866,236, filed on Aug. 15, 2013.

(51) Int. Cl.
| | |
|---|---|
| *A61B 1/00* | (2006.01) |
| *A61B 19/00* | (2006.01) |
| *A61B 34/00* | (2016.01) |
| *A61B 34/30* | (2016.01) |
| *A61B 17/00* | (2006.01) |

(52) U.S. Cl.
CPC .......... *A61B 19/2203* (2013.01); *A61B 34/30* (2016.02); *A61B 34/71* (2016.02); *A61B 2017/00477* (2013.01); *A61B 2034/306* (2016.02)

(58) Field of Classification Search
CPC ...... A61B 19/2203; A61B 34/30; A61B 34/71
See application file for complete search history.

(56) References Cited

U.S. PATENT DOCUMENTS

| | | | | |
|---|---|---|---|---|
| 3,967,997 A | * | 7/1976 | Masters | H01B 13/016 156/201 |
| 4,090,896 A | * | 5/1978 | Myers | B29C 47/02 156/498 |
| 4,368,976 A | * | 1/1983 | Shogren | G03G 15/041 355/55 |
| 4,899,988 A | * | 2/1990 | Mills | B65H 51/04 254/134.3 R |
| 5,280,879 A | * | 1/1994 | Kreuter | B61B 12/10 254/333 |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — David M Fenstermacher

(57) ABSTRACT

A force transmission includes an input axle having an input axis of rotation that receives a rotational input. An input capstan is fixed to the input axle. An output capstan is fixed to a main tube bushing. The output capstan and main tube bushing have an output axis of rotation that is at an angle to the input axis of rotation. A cable couples the rotation of the input capstan to rotate the output capstan and the main tube bushing. At least one of the input capstan and the output capstan is tapered such that the overall path length of the cable remains substantially the same throughout the range of motion of the capstans.

18 Claims, 3 Drawing Sheets

(56) References Cited

U.S. PATENT DOCUMENTS

| | | | |
|---|---|---|---|
| 7,228,582 B1* | 6/2007 | Jones | B63B 27/143 |
| | | | 14/69.5 |
| 2002/0017122 A1* | 2/2002 | McCabe | B21C 1/02 |
| | | | 72/289 |
| 2008/0009838 A1* | 1/2008 | Schena | A61B 34/71 |
| | | | 606/1 |
| 2010/0082041 A1* | 4/2010 | Prisco | B25J 9/1045 |
| | | | 606/130 |

* cited by examiner

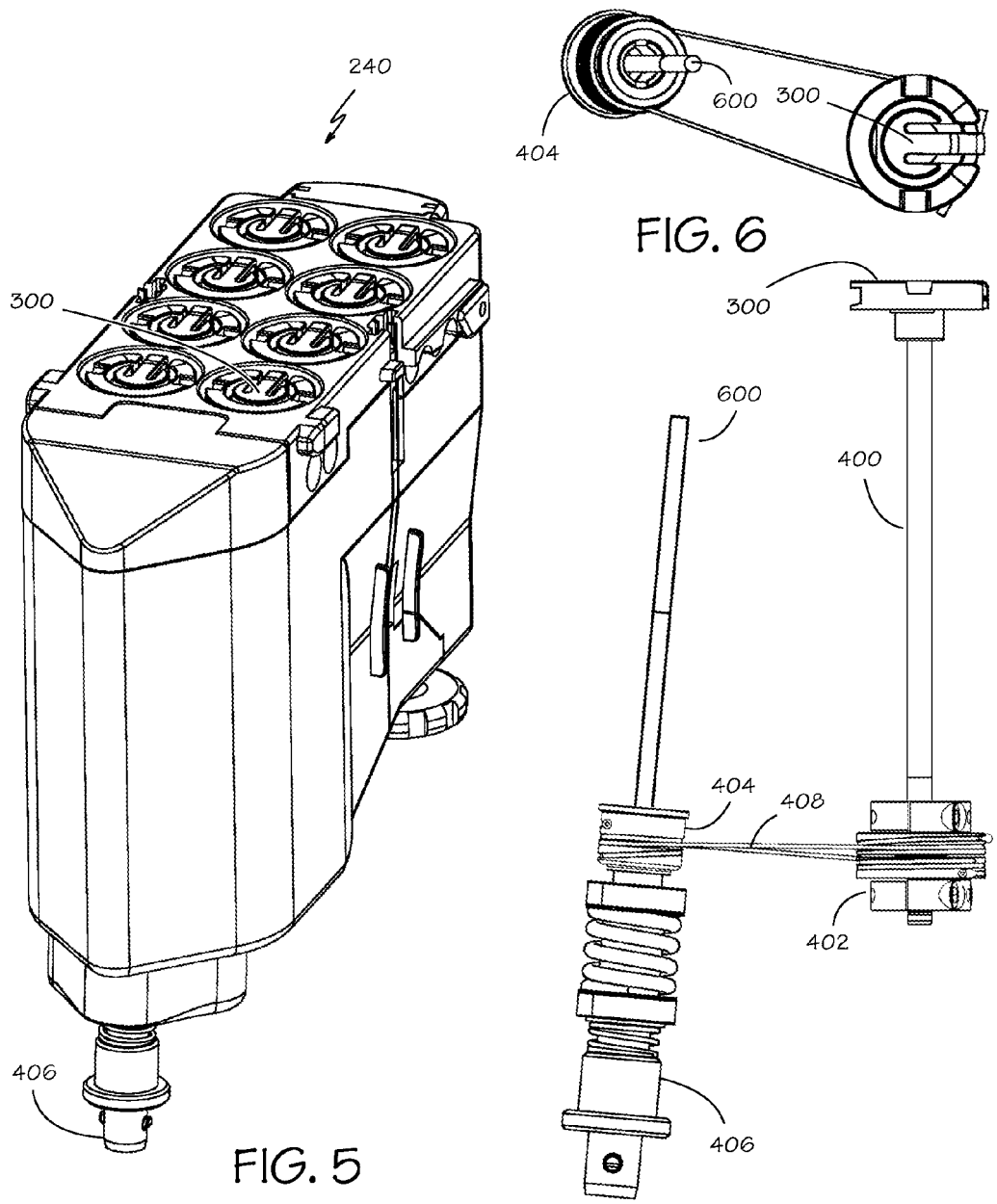
FIG. 6
FIG. 5
FIG. 7
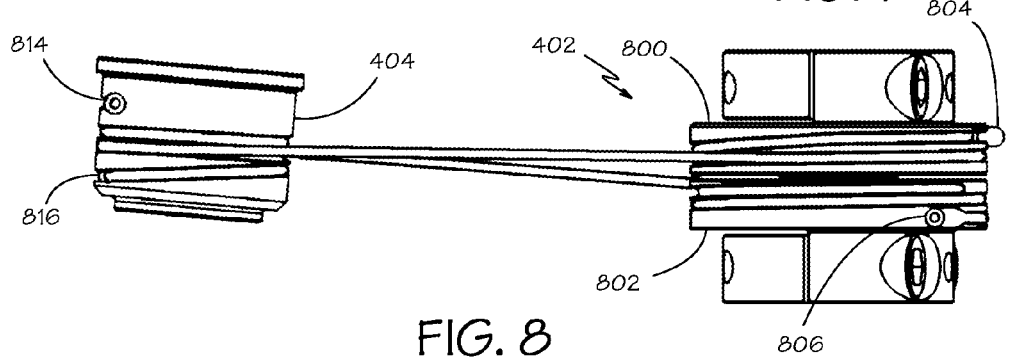
FIG. 8

ANGLED INSTRUMENT SHAFT ROLL ACTUATOR

BACKGROUND

Field

Embodiments of the invention relate to the field of force transmissions; and more specifically, to force transmissions for use in surgical instruments intended for use in teleoperated minimally invasive surgeries.

Background

Minimally invasive surgery (MIS) (e.g., endoscopy, laparoscopy, thoracoscopy, cystoscopy, and the like) allows a patient to be operated upon through small incisions by using elongated surgical instruments introduced to an internal surgical site. Generally, a cannula is inserted through the incision to provide an access port for the surgical instruments. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor. In teleoperated minimally invasive surgery, the surgeon manipulates the tissues by controlling mechanically actuated end effectors of the elongated surgical instruments with a computer mediated control console. Mechanical actuation may allow for improved control of the surgical instruments.

The mechanically actuated surgical instruments will generally have an end effector in the form of a surgical tool such as a forceps, a scissors, a clamp, a needle grasper, or the like at a distal end of an elongate tube. The surgical tool is generally coupled to the elongate tube by one or more articulated sections. The elongate tube is rotated to control the orientation of the surgical tool. An actuator that provides the actuating forces to rotate the elongate tube is coupled to the proximal end of the elongate tube. It may be desirable that the elongate tube be at an angle to the actuators at the proximal end of the elongate tube so that several surgical tools may converge at a surgical site despite the inability to have the proximal ends of the elongate tubes converge because of the bulk of the actuators.

In view of the above, it is desirable to provide an improved apparatus and method for transmitting actuating forces to rotate an elongate tube of a surgical instrument intended for use in teleoperated minimally invasive surgeries where the elongate tube is at an angle to the actuator.

SUMMARY

A force transmission includes an input axle having an input axis of rotation that receives a rotational input. An input capstan is fixed to the input axle. An output capstan is fixed to a main tube bushing. The output capstan and main tube bushing have an output axis of rotation that is at an angle to the input axis of rotation. A cable couples the rotation of the input capstan to rotate the output capstan and the main tube bushing. At least one of the input capstan and the output capstan is tapered such that the overall path length of the cable remains substantially the same throughout the range of motion of the capstans.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 5 is a perspective view of the surgical instrument of FIG. 2.

FIG. 6 is a top view of a portion of the surgical instrument of FIG. 2 that provides a roll drive for the elongate tube of the surgical instrument.

FIG. 7 is a side view of the portion of the surgical instrument of FIG. 6.

FIG. 8 is a enlarged view of the capstans of the surgical instrument of FIG. 7.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
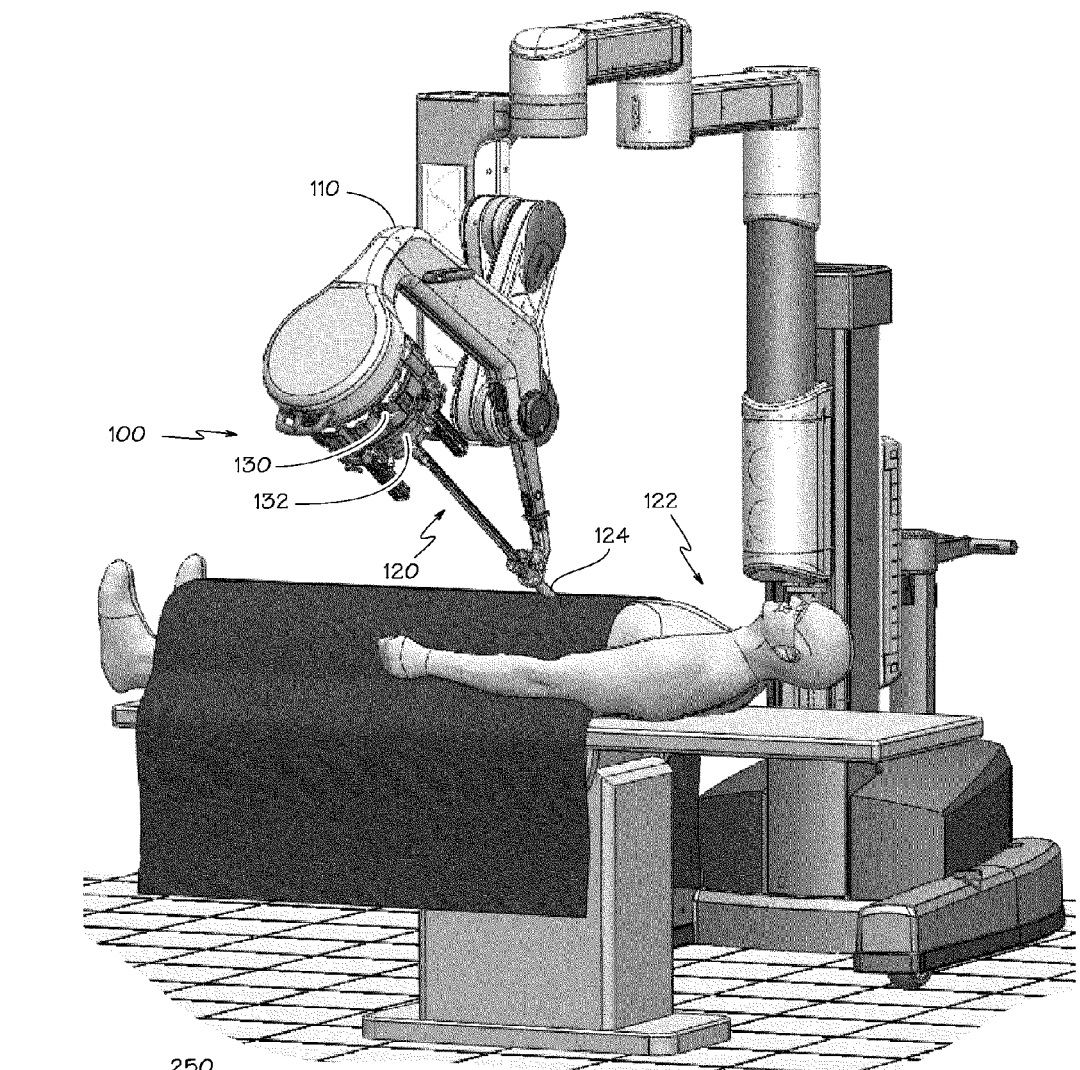
FIG. 1 is a simplified perspective view of a teleoperated surgical system with a mechanically actuated surgical instrument inserted through a port in a patient's abdomen.

FIG. 1 is a simplified diagrammatic perspective view of a teleoperated surgical system 100. The system 100 includes a support assembly 110 mounted to or near an operating table supporting a patient's body 122. The support assembly 110 supports one or more surgical instruments 120 that operate on a surgical site within the patient's body 122.

The term "instrument" is used herein to describe a device configured to be inserted into a patient's body and used to carry out surgical procedures. The instrument includes a surgical tool, such as a forceps, a needle driver, a shears, a monopolar cauterizer, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support for the surgical tool so that the position and orientation of the surgical tool can be manipulated.

The simplified perspective view of the system 100 shows only a single instrument 120 to allow aspects of the invention to be more clearly seen. A functional teleoperated surgical system would further include a vision system that enables the operator to view the surgical site from outside the patient's body 122. The vision system can include a video monitor for displaying images received by an optical device provided at a distal end of one of the surgical instruments 120. The optical device can include a lens coupled to an optical fiber which carries the detected images to an imaging sensor (e.g., a CCD or CMOS sensor) outside of the patient's body 122. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the DA VINCI® Surgical System, marketed by Intuitive Surgical, Inc., of Sunnyvale Calif.

A functional teleoperated surgical system would further include a control system for controlling the insertion and articulation of the surgical instruments 120. This control may be effectuated in a variety of ways, depending on the degree of control desired, the size of the surgical assembly, and other factors. In some embodiments, the control system includes one or more manually operated input devices, such as a joystick, exoskeletal glove, or the like. These input devices control motors, such as servo motors, which, in turn, control the articulation of the surgical assembly. The forces generated by the motors are transferred via drivetrain mechanisms, which transmit the forces from the motors generated outside the patient's body 122 through an intermediate portion of the elongate surgical instrument 120 to a portion of the surgical instrument inside the patient's body 122 distal from the motor. Persons familiar with telemanipulative, teleoperative, and telepresence surgery will know of systems such as the DA VINCI® Surgical System and the ZEUS® Surgical System originally manufactured by Computer Motion, Inc. and various illustrative components of such systems.

The surgical instrument 120 is shown inserted through an entry guide 124, e.g., a cannula in the patient's abdomen. A functional teleoperated surgical system may provide an entry guide manipulator (not shown; in one illustrative aspect the entry guide manipulator is part of the support system 110) and an instrument manipulator (discussed below). The entry guide 124 is mounted onto the entry guide manipulator, which includes a mechanically actuated positioning system for positioning the distal end of the entry guide 124 at the desired target surgical site. The mechanically actuated positioning system may be provided in a variety of forms, such as a serial link arm having multiple degrees of freedom (e.g., six degrees of freedom) or a jointed arm that provides a remote center of motion (due to either hardware or software constraints) and which is positioned by one or more unpowered, lockable setup joints mounted onto a base. Alternatively, the entry guide manipulator may be manually maneuvered so as to position the entry guide 124 in the desired location. In some telesurgical embodiments, the input devices that control the manipulator(s) may be provided at a location remote from the patient (outside the room in which the patient is placed). The input signals from the input devices are then transmitted to the control system, which, in turn, manipulates the manipulators 130 in response to those signals. The instrument manipulator may be coupled to the entry guide manipulator such that the instrument manipulator 130 moves in conjunction with the entry guide 124.

The surgical instrument 120 is detachably connected to the mechanically actuated instrument manipulator 130. The mechanically actuated manipulator includes a coupler 132 to transfer controller motion from the mechanically actuated manipulator to the surgical instrument 120. The instrument manipulator 130 may provide a number of controller motions which the surgical instrument 120 may translate into a variety of movements of the end effector on the surgical instrument such that the input provided by a surgeon through the control system is translated into a corresponding action by the surgical instrument.

Figure 2:
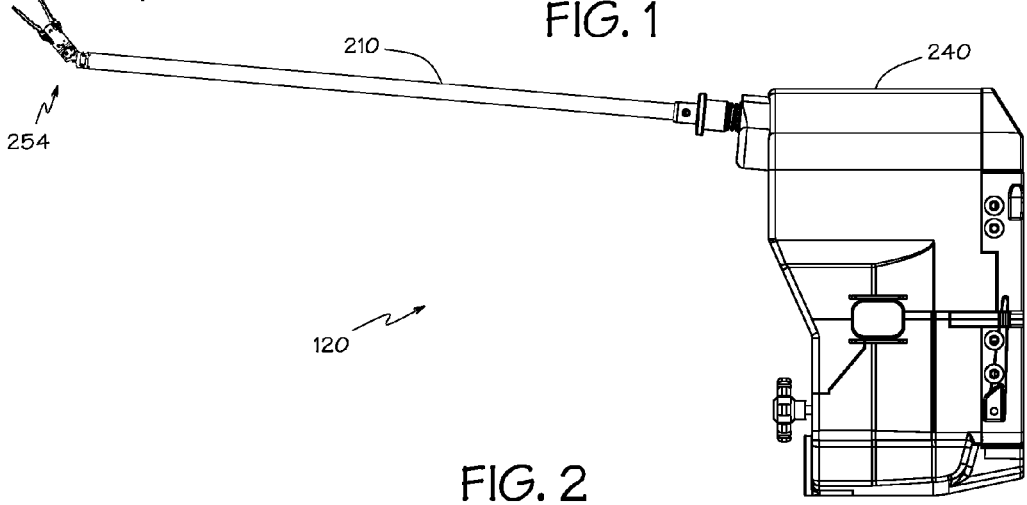
FIG. 2 is a plan view of a surgical instrument for use with a mechanically actuated manipulator.

FIG. 2 is a plan view of an illustrative embodiment of the surgical instrument 120, comprising a distal portion 250 and a proximal control mechanism 240 coupled by an elongate tube 210. The distal portion 250 of the surgical instrument 120 may provide any of a variety of surgical devices such as the forceps 258 shown, a needle driver, a cautery device, a cutting tool, an imaging device (e.g., an endoscope or ultrasound probe), or a combined device that includes a combination of two or more various tools and imaging devices. In the embodiment shown, the surgical tool 258 is coupled to the elongate tube 210 by an articulated section in the form of a "wrist" 254 that allows the orientation of the surgical tool to be manipulated. Surgical instruments that are used with the invention provide a mechanism for rotating the elongate tube 210 to provide a roll motion of the surgical tool 258.

Figure 3:
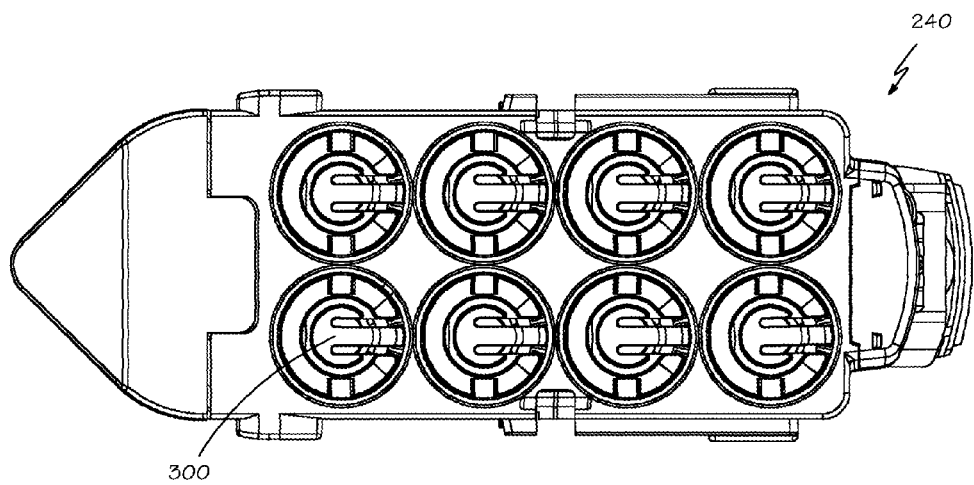
FIG. 3 is a top view of the surgical instrument of FIG. 2 showing the input connections that connect to actuators.

FIG. 3 is a top view of the proximal control mechanism 240 for the surgical instrument of FIG. 2 showing the input connections 300 that connect to actuators (not shown). The actuators used with embodiments of the invention are rotary actuators, such as servo motors. The proximal control mechanism of the surgical instrument may provide input connections for a number of actuators with each actuator controlling or partially controlling one motion of the surgical tool. For example, the proximal control mechanism 240 shown provides eight input connections 300. Of course, some input connections may be unused by some surgical instruments.

Figure 4:
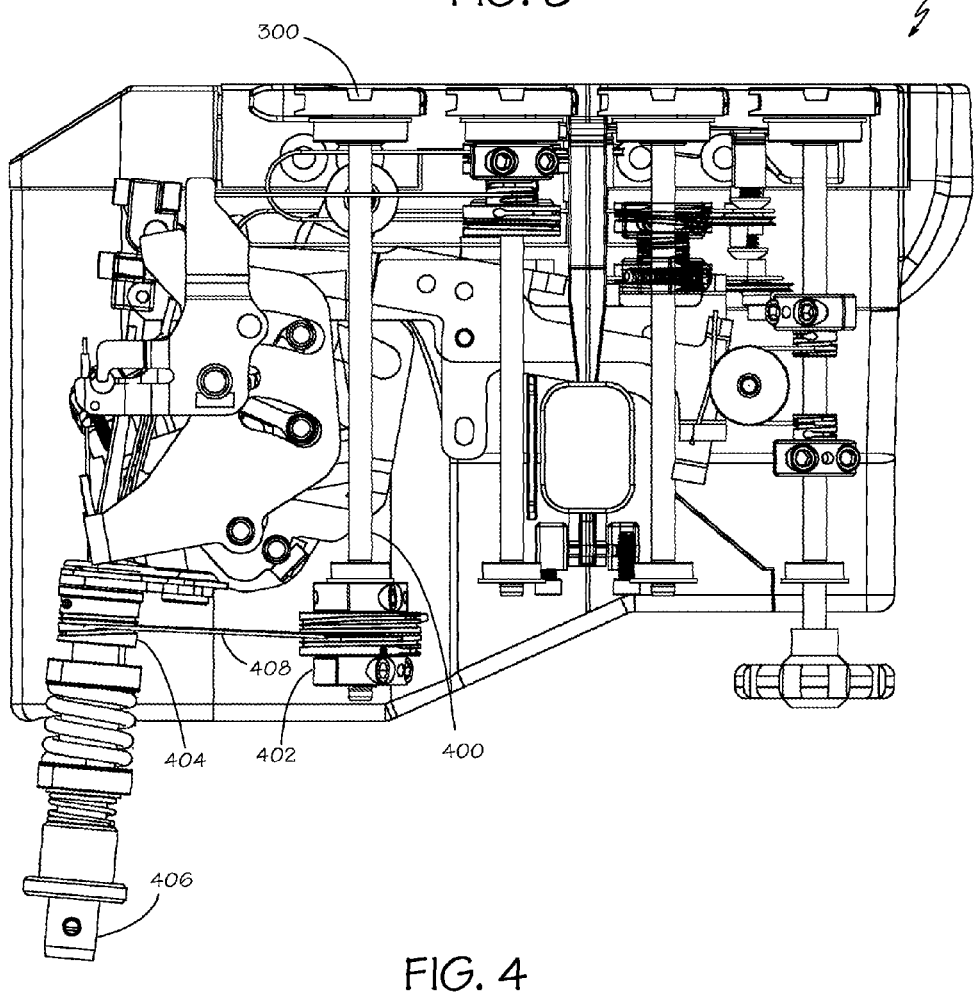
FIG. 4 is a side view of the surgical instrument of FIG. 2 with portions of the housing and support structure removed to show a mechanism for driving a mechanically actuated surgical instrument.

FIG. 4 is a side view of the proximal control mechanism 240 for the surgical instrument of FIG. 2 with portions of the housing and support structure removed to show a mechanism for driving a mechanically actuated surgical instrument. One of the input connections 300 is fixed to an input axle 400 having an input axis about which the input connection rotates. The input axle receives a rotational input from an actuator that is removably coupled to the input connection 300. An input capstan 402 is fixed to the input axle 400.

The proximal control mechanism 240 holds the elongate tube (210 of FIG. 2) in a main tube bushing 406. The main tube bushing 406 has an output axis about which the main tube bushing and the held elongate tube rotate. The output axis of the main tube bushing 406 is at an angle, such as 5°, to the input axis of the input axle 400. When several proximal control mechanisms 240 are arranged in close proximity, the bulk of the mechanism and the associated actuators requires the main tube bushings 406 to be somewhat spaced apart. The angled orientation of the main tube bushing 406 assists in converging the distal ends of the elongate tubes at a surgical site.

An output capstan 404 is fixed to the main tube bushing 406. A cable 408 couples the rotation of the input capstan 402 to rotate the output capstan 404 and the main tube bushing 406. The capstans preferably include helical grooves to guide the winding of the cable on the capstans. It will be appreciated that as the capstans turn, the cable takeoff points on the capstans translate along the length of the axes of rotation of the capstans according to the pitch of the helical cable guide grooves.

FIG. 5 is a perspective view of the surgical instrument of FIG. 2. It should be noted that some proximal control mechanisms 240, such as the one illustrated, provide actuator inputs that are offset from the midplane of the control mechanism while the axis of rotation for the main tube bushing 406 is located on the midplane. Since the input axis is at an angle to the output axis and the two axes lie in different planes in the illustrated proximal control mechanism 240, the input axis does not intersect the output axis.

FIG. 6 is a top view and FIG. 7 is a side view of a portion of the surgical instrument of FIG. 2 that provides a roll drive for the elongate tube 600 of the surgical instrument. Note that only the distal end of the elongate tube 600 is shown. The portion of the elongate tube that projects from the main tube bushing 406 toward the surgical site is not shown. In some embodiments, the input capstan may have a different diameter than the output capstan. For example, in the embodiment shown in the figures the gear ratio of the input diameter of the input capstan 402 to the output diameter of the output capstan 404 is 3:2.

If the pitch ratio of the input pitch of cable guide grooves on the input capstan to the output pitch of cable guide grooves on the output capstan is the same as the gear ratio, then fleet angle at which the cable takes off from the capstans will not change as the capstans rotate. For example, in the embodiment shown in the figures the input pitch is 0.06 inches and the output pitch is 0.04 inches, which provides the same 3:2 ratio as the gear ratio of the capstan diameters.

FIG. 8 is a enlarged view of the capstans of the surgical instrument of FIG. 7. In some embodiments the cable consists of two segments, each segment being fixed at one end 804, 806 to the input capstan 402 and fixed at an opposite end 814, 816 to the output capstan 404, as illustrated. In such embodiments the input capstan 402 may comprise two portions 800, 802. Each portion of the input capstan 402 may be separately fixed to the input axle 400. Each of the two segments of the cable is then fixed to a different portion 800, 802 of the input capstan. In such embodiments each portion 800, 802 of the input capstan 402 can be rotated to adjust the tension in the portion of the cable fixed to that portion of the input capstan before that portion of the input capstan is fixed to the input axle 400. It will be appreciated that the output capstan 404 may comprise two portions to provide an adjustment of the tension in the attached portion of the cable.

Since the output axis is at an angle to the input axis, the distance between the cable takeoff points from the capstans will change as the cable takeoff points translate. Thus it is necessary to provide a mechanism to compensate for the changing distance between the cable takeoff points to maintain cable tension for proper rotation of the main tube bushing 406 by the actuator coupled to the proximal control mechanism 240.

The change of cable length as a function of the translation of the takeoff points was determined by graphical methods for an exemplary proximal control mechanisms 240 with a geometry as illustrated by the figures and having the exemplary dimensions described above:

| translation | length | delta |
| --- | --- | --- |
| 0.00 | 4.5065 | 0.0000 |
| 0.01 | 4.5049 | 0.0016 |
| 0.02 | 4.5032 | 0.0033 |
| 0.03 | 4.5015 | 0.0050 |
| 0.04 | 4.4998 | 0.0067 |
| 0.05 | 4.4982 | 0.0083 |
| 0.06 | 4.4965 | 0.0100 |
| 0.07 | 4.4948 | 0.0117 |
| 0.08 | 4.4931 | 0.0134 |
| 0.09 | 4.4915 | 0.0150 |
| 0.10 | 4.4898 | 0.0167 |

From the foregoing data it was observed that the change of cable length was a substantially linear function of the translation of the takeoff points. It was then determined that providing a tapered output capstan 404 in which each side was tapered by 3° would result in a change in the length of the portion of the cable wound on the capstans to substantially offset the change in the length of the portion of the cable between the capstans as the input capstan 402 and the output capstan 404 rotate.

It will be appreciated that either the input capstan or the output capstan can be tapered to maintain cable tension between capstans whose axes of rotation are at an angle to one another. Further, it is desirable to taper both capstans to maintain a constant gear ratio between the capstans although the change in gear ratio over the range of motion may be small for drive geometries such as the one illustrated.

In general, tension can be maintained in a cable drive between capstans whose axes of rotation are at an angle to one another if at least one of the input capstan and the output capstan is tapered. The distance between the input capstan and the output capstan take-off points changes as the input capstan and the output capstan rotate and the cable translates along the capstans. The taper causes a circumference for at least one of the capstans to change as the cable translates along capstan. This change in circumference can substantially offset the changes in the distance between the input capstan and the output capstan take-off points and keep the length of the overall path of the cable substantially the same throughout the range of motion of the capstans. Thus the need to keep the axes of rotation parallel or provide a cable tensioning mechanism can be eliminated.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A force transmission comprising:
an input axle having an input axis, the input axle receiving a rotational input;
an input capstan fixed to the input axle;
a main tube bushing having an output axis that is at an acute angle of at least 5 degrees to the input axis;
an output capstan fixed to the main tube bushing; and
a cable that couples rotation of the input capstan to rotate the output capstan and the main tube bushing;
wherein at least one of the input capstan and the output capstan is tapered such that an overall path length of the cable remains substantially the same throughout a range of motion of the input capstan and the output capstan.

2. The force transmission of claim 1 wherein the input capstan has a different diameter than the output capstan.

3. The force transmission of claim 2 wherein a pitch ratio of an input pitch of the input capstan to an output pitch of the output capstan is the same as a gear ratio of an input diameter of the input capstan to an output diameter of the output capstan.

4. The force transmission of claim 1 wherein the main tube bushing is configured to support an elongate tube of a mechanically actuated surgical instrument.

5. The force transmission of claim 1 wherein the cable consists of two segments, each segment being fixed at one end to the input capstan and fixed at an opposite end to the output capstan.

6. The force transmission of claim 5 wherein one or both of the input capstan and the output capstan comprises two capstan portions, each capstan portion being separately fixed and each of the two segments of the cable being attached to different capstan portions.

7. A force transmission comprising:
means for receiving a rotational input;
an input capstan fixed to the means for receiving the rotational input, the input capstan rotating about an input axis;
means for rotating a mechanically actuated surgical instrument;
an output capstan fixed to the means for rotating the mechanically actuated surgical instrument, the output capstan rotating about an output axis that is at an acute angle of at least 5 degrees to the input axis; and
a cable for transferring rotation of the input capstan to the output capstan, wherein at least one of the input capstan and the output capstan is tapered such that an overall path length of the cable remains substantially the same throughout a range of motion of the input capstan and the output capstan.

8. The force transmission of claim 7 wherein the input capstan has a different diameter than the output capstan.

9. The force transmission of claim 8 wherein a pitch ratio of an input pitch of the input capstan to an output pitch of the output capstan is the same as a gear ratio of an input diameter of the input capstan to an output diameter of the output capstan.

10. The force transmission of claim 7 wherein the means for rotating the mechanically actuated surgical instrument is configured to support an elongate tube of the mechanically actuated surgical instrument.

11. The force transmission of claim 7 wherein the cable consists of two segments, each segment being fixed at one end to the input capstan and fixed at an opposite end to the output capstan.

12. The force transmission of claim 11 wherein one or both of the input capstan and the output capstan comprises two capstan portions, each capstan portion being separately fixed and each of the two segments of the cable being attached to different capstan portions.

13. A method of transmitting force to a mechanically actuated surgical instrument, the method comprising:
receiving a rotational force input on an input axle having an input axis and an input capstan fixed to the input axle; and
transferring the rotational force input to a main tube bushing having an output axis that is at an acute angle of at least 5 degrees to the input axis by a cable that couples rotation of the input capstan to rotate an output capstan fixed to the main tube bushing;
wherein at least one of the input capstan and the output capstan is tapered such that an overall path length of the cable remains substantially the same throughout a range of motion of the input capstan and the output capstan.

14. The method of claim 13 wherein the input capstan has a different diameter than the output capstan.

15. The method of claim 14 wherein a pitch ratio of an input pitch of the input capstan to an output pitch of the output capstan is the same as a gear ratio of an input diameter of the input capstan to an output diameter of the output capstan.

16. The method of claim 13 further comprising supporting an elongate tube of the mechanically actuated surgical instrument with the main tube bushing.

17. The method of claim 13 wherein the cable consists of two segments, each segment being fixed at one end to the input capstan and fixed at an opposite end to the output capstan.

18. The method of claim 17 wherein one or both of the input capstan and the output capstan comprises two capstan portions, each capstan portion being separately fixed and each of the two segments of the cable being attached to different capstan portions, the method further comprising rotating each capstan portion to adjust a tension in the attached cable segment before that capstan portion is fixed.

* * * * *